United States Patent
Wells

[54] BALL JOINT RETRACTOR

[75] Inventor: B. Keith Wells, Marietta, Ga.

[73] Assignee: Genzyme Corporation, Framingham, Mass.

[21] Appl. No.: 09/169,683

[22] Filed: Oct. 9, 1998

Related U.S. Application Data

[63] Continuation of application No. 08/934,626, Sep. 19, 1997.

[51] Int. Cl.⁶ .................................................. A61B 17/00
[52] U.S. Cl. ............................................................ 600/226
[58] Field of Search ................................... 600/201, 210, 600/221, 226, 185, 190, 194

[56] References Cited

U.S. PATENT DOCUMENTS

| | | |
|---|---|---|
| 2,670,732 | 8/1954 | Nelson . |
| 2,693,795 | 11/1954 | Grieshaber ............................. 600/213 |
| 2,863,444 | 12/1958 | Winsten .................................. 600/214 |
| 3,030,948 | 8/1962 | Loeffler . |
| 3,196,865 | 7/1965 | Rose . |
| 3,221,743 | 12/1965 | Thompson et al. ...................... 128/303 |
| 3,409,013 | 11/1968 | Berry .................................. 600/201 X |
| 3,467,079 | 9/1969 | James . |
| 3,882,855 | 5/1975 | Schulte et al. ....................... 600/201 X |
| 4,050,464 | 9/1977 | Hall ........................................ 128/303 |
| 4,052,980 | 10/1977 | Grams et al. ........................ 600/211 X |
| 4,151,838 | 5/1979 | Crew . |
| 4,323,057 | 4/1982 | Jamieson . |
| 4,457,300 | 7/1984 | Budde ..................................... 600/228 |
| 4,616,634 | 10/1986 | Vargas Garcia .......................... 600/210 |
| 4,949,707 | 8/1990 | LeVahn et al. ...................... 600/228 X |
| 5,133,724 | 7/1992 | Wilson, Jr. et al. ..................... 606/151 |
| 5,167,223 | 12/1992 | Koros et al. ............................. 600/232 |
| 5,201,325 | 4/1993 | McEwen et al. ......................... 428/779 |
| 5,318,013 | 6/1994 | Wilk .................................... 600/225 X |
| 5,337,736 | 8/1994 | Reddy ..................................... 600/217 |
| 5,429,118 | 7/1995 | Cole et al. ............................... 600/121 |
| 5,449,374 | 9/1995 | Dunn et al. .......................... 600/214 X |
| 5,498,256 | 3/1996 | Furnish ..................................... 606/1 |
| 5,509,890 | 4/1996 | Kazama ..................................... 600/37 |
| 5,512,037 | 4/1996 | Russell et al. ........................... 600/206 |
| 5,514,076 | 5/1996 | Ley ......................................... 600/206 |
| 5,514,077 | 5/1996 | Rabban .................................... 600/226 |
| 5,529,571 | 6/1996 | Daniel ................................. 600/213 X |
| 5,554,101 | 9/1996 | Matula et al. ........................... 600/214 |
| 5,558,621 | 9/1996 | Heil .................................... 600/201 X |
| 5,588,951 | 12/1996 | Zhu et al. ................................ 600/207 |

[11] Patent Number: 5,904,650

[45] Date of Patent: May 18, 1999

FOREIGN PATENT DOCUMENTS

| | | | |
|---|---|---|---|
| 2233561 | 1/1991 | United Kingdom ................... | 600/234 |

*Primary Examiner*—Jeffrey A. Smith
*Attorney, Agent, or Firm*—Needle & Rosenberg

[57] ABSTRACT

A retractor comprising a longitudinally-extending blade having a top surface, a bottom surface, a distal end, and an opposed proximal end, a receptacle adapted to support a predetermined surgical instrument and disposed adjacent the bottom surface of the blade, a handle fixedly attached to the blade and defining a bore extending therethrough, and a ball disposed within the bore of the handle. A portion of the ball is fixedly attached to a portion of the receptacle and secured within the bore of the handle so that the ball and attached receptacle are movable relative to the blade without separating therefrom to a selected one of a plurality of desired positions. The retractor also comprises a shaft complementarily received within the bore, the lower end of the shaft is sized to complementarily and detachably engage a portion of the ball. The shaft is adjustably positionable within the bore between an engaged position, in which the shaft detachably engages the ball to frictionally hold the ball, and a disengaged position, in which the shaft and the ball are spaced apart so that the ball is movable within the bore.

5 Claims, 2 Drawing Sheets

BALL JOINT RETRACTOR

This application is a continuation of, and claims the benefit of, application Ser. No. 08/934,626, filed Sep. 19, 1997, which status is pending, which application is hereby incorporated herein by reference.

BACKGROUND OF THE INVENTION

1. Field of the Invention

The present invention relates generally to the field of surgical instrumentation and, more particularly, to surgical retractors adapted for endoscopic use. Even more specifically, the present invention relates to a retractor having a ball joint movably connecting the retractor to a receptacle which supports an endoscopic surgical device.

2. Background Art

Retractors are well suited for use with endoscopic surgical instruments used to perform examinations or surgical procedures within body cavities. An endoscopic camera is often placed within the surgical site, in which the output of the camera is displayed on a video monitor. The surgeon monitors the organ or internal tissue subject to inspection, repair, dissection, or excision on the video monitor, instead of directly viewing the site as occurs in conventional surgery. In conjunction, the surgeon guides other endoscopic instruments (such as a grasper, a hook, a spatula, forceps, a dissector, and the like for performing specific surgical functions) into and out of the operating site through respective surgical sheaths. When the distal tip of the instrument appears on the video monitor, the surgeon guides the instrument into place and controls its action and movement while monitoring the video monitor. Use of endoscopic visualization to monitor of the body cavity in which the surgical procedure occurs minimizes scarring, allows a quicker recovery, and reduces the risk to the patient.

Endoscopic visualization, however, can be difficult because of insufficient suitable working space due to impingement of surrounding tissues. This problem can be more pronounced in obese patients. Also, the surgeon sometimes must reposition the endoscope to continue viewing the operative site during the course of the surgical procedure. That is, the physical location where the surgical procedure occurs can shift during the operation and the endoscope must be moved accordingly. Prior art retractors that support an endoscope are not equipped to move the endoscope without shifting the entire retractor, which can increase the trauma to the contacted tissue.

Therefore, a need exists in the art for a retractor that can be used in conjunction with an endoscope, in which the retractor allows movement of the endoscopic camera to numerous positions within the body cavity without moving the entire retractor. However, there is also a desire to have the endoscopic camera supported by the retractor, allowing the surgeons and assistants to attend to other matters instead of holding the camera. The prior art does not satisfy this need.

Another need in the art is for the surgeon to be able to lock quickly the endoscopic camera once it is at the desired orientation relative to the retractor. It is preferred that the surgeon be able to lock the camera in the desired position by using one finger on the hand which is holding and moving the retractor. Thus, the surgeon would not also need to use his other hand in addition to the one already supporting the retractor.

SUMMARY OF THE INVENTION

The present invention satisfies the needs in the art. The present invention comprises a retractor that movably supports an endoscope or other surgical instrument. More specifically, the present invention comprises a retractor having a longitudinally extending blade, a receptacle adapted to support a predetermined surgical instrument (such as an endoscope), and a means for movably connecting the receptacle to the blade.

The receptacle and supported surgical instrument are moveable relative to the blade to a selected one of a plurality of desired positions without moving the blade. The present invention also preferably further comprises a means for detachably locking the receptacle at the selected desired position, i.e., the position in which the endoscope is oriented at the desired location. The preferred embodiment of the connecting means comprises a ball and socket design, in which the shaft moves the socket either to lock or unlock the ball.

The preferred receptacle comprises a longitudinally-extending tube defining a passage therethrough. The passage is of a size to allow the preferred endoscopic instrument to be slidably received therein so that the distal end of the instrument protrudes from or is aligned with the distal end of the tube. It is contemplated that surgical instruments can be switched during the surgical procedure while stationarily maintaining the blade at the surgical site. Thus, the surgeon can switch the surgical instrument and then reposition the new instrument, while the blade remains stationary at the surgical site.

The surgeon can easily maneuver the endoscopic camera supported by the retractor and lock the camera into position at a desired location. This allows the surgeon or surgical assistants to attend to other matters instead of holding the camera.

It is, therefore, an object of the present invention to provide a hand-held retractor that is adapted for endoscopic use at a predetermined area inside of a patient, which allows a surgeon access to and visualization of the predetermined area while protecting adjacent structures. More particularly, it is an object of the present invention to provide a retractor that is adapted for endoscopic use which has a low-profile design to facilitate work in the body cavity.

Yet another object of the present invention is to provide a retractor that can be used in conjunction with an endoscope, in which endoscope is movable to numerous positions within the body cavity (i.e., up and down, side to side, and a combination thereof relative to the blade) without moving the blade itself.

Still another object of the invention is to allow the surgeon to lock the endoscopic camera into position quickly and easily.

The above recited objects of the invention are not intended to limit the scope of the invention. These and other objects of the invention will be apparent to the skilled artisan based upon the following disclosure.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used. The preferred embodiment is now described with reference to the figures, in which like numbers indicate like parts throughout the figures.

Figure 1:
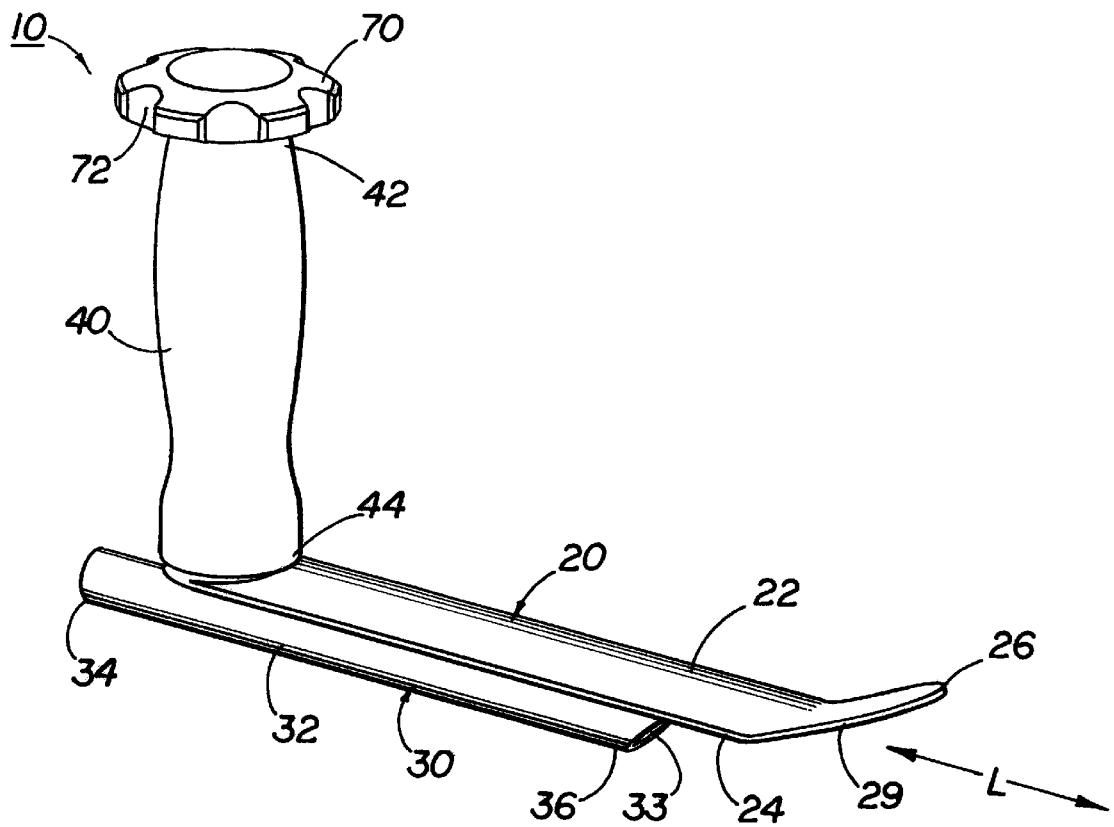
FIG. 1 is a front perspective view of the preferred embodiment of the present invention.
Figure 2:
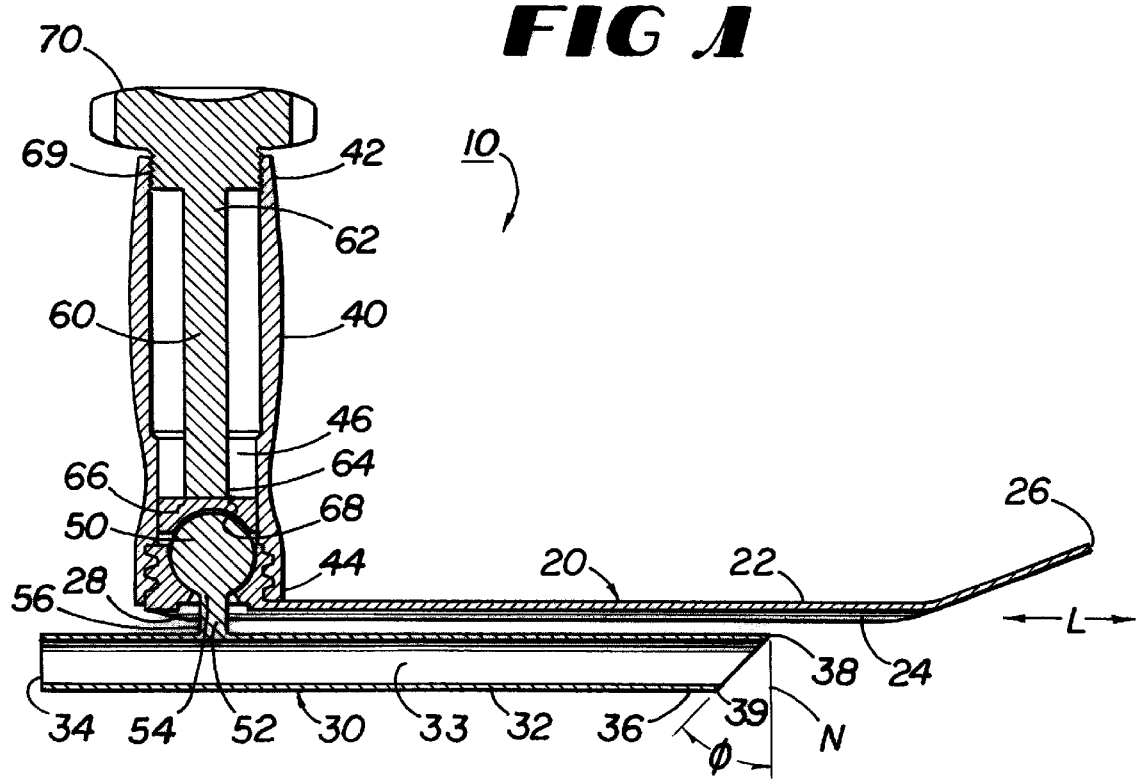
FIG. 2 is a side cross-sectional view of FIG. 1.
Figure 3:
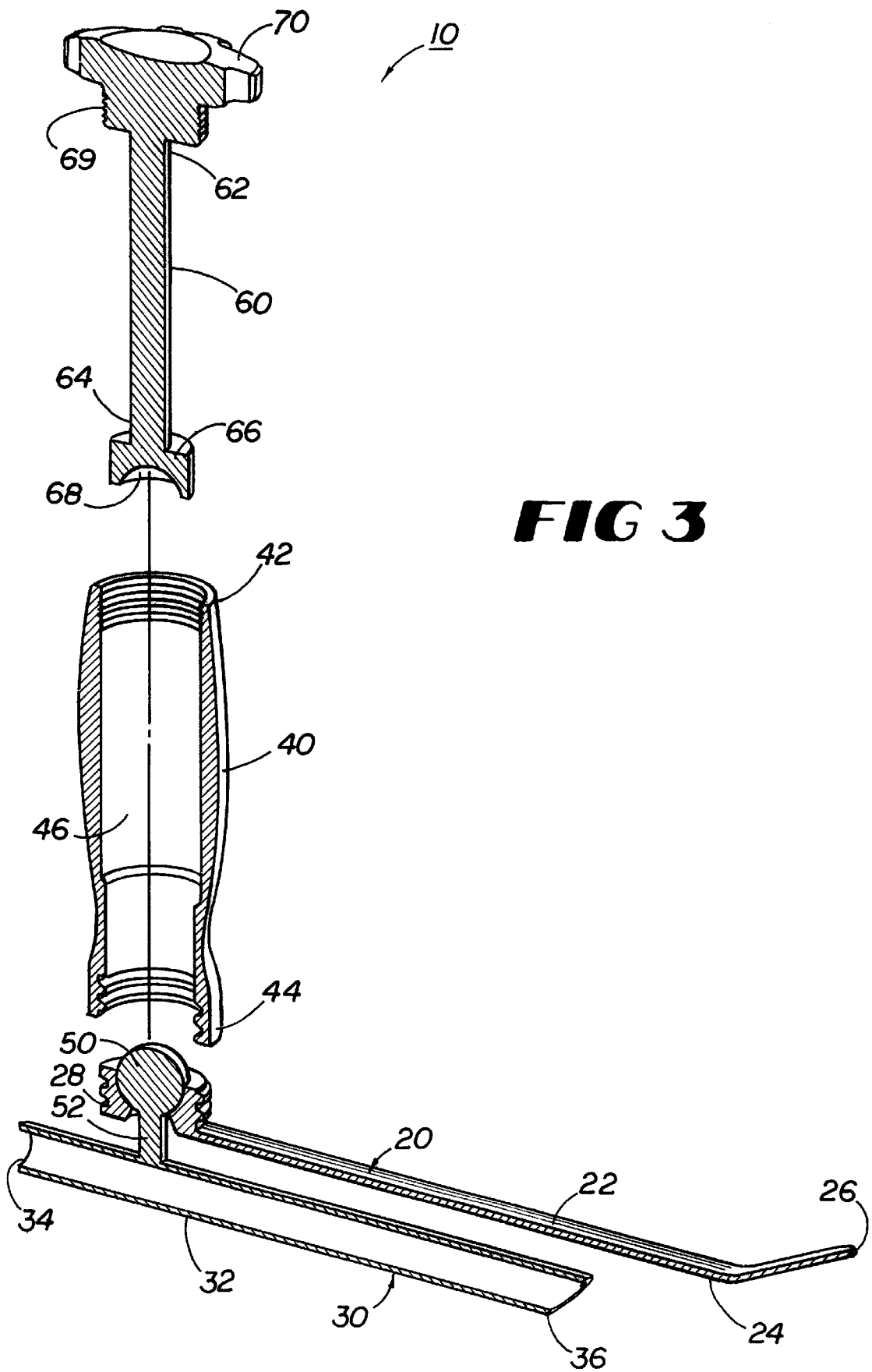
FIG. 3 is an exploded side cross-sectional view of FIG. 1.

Referring to FIGS. 1–3, the present invention comprises a retractor 10 having a longitudinally-extending blade 20, a receptacle 30 adapted to support a predetermined surgical instrument (not shown), and a means for movably connecting the receptacle 30 to the blade 20. The connecting means allows the receptacle 30, and supported surgical instrument, to move relative to the blade 20 to a selected one of a plurality of desired positions. The connecting means also enables movement of the receptacle 30, whenever necessary, such as if the location of the predetermined surgical instrument must be moved to another portion of the body cavity during the surgery. In addition, the retractor 10 preferably further comprises a means for detachably locking the receptacle 30 at the selected desired position. The selected desired position can be, for example, the position in which the endoscope is focused on the surgical site.

One use of the retractor 10 of the present invention is for preforming breast augmentation or reduction surgical procedures. The retractor 10 can be used for other operations, such as abdominal surgery, lysis of intra-uterine adhesions or other thoracic adhesions, and the like. The retractor 10 is particularly advantageous when using endoscopic visualization, in which the predetermined surgical instrument is a combined endoscope and light source supported by the receptacle 30.

The blade 20 of the retractor 10 has a longitudinal axis L, a top surface 22, a bottom surface 24, a distal end 26, an opposed proximal end 28, and an edge 29 circumscribing it. The preferred material to construct the retractor 10 is a stainless steel or a biocompatable alloy that is acceptable for surgery. However, other materials are also contemplated, such as plastic.

The preferred length of the blade 20 extending between the distal and proximal ends 26, 28 can vary depending on the specific surgical site and the size of the patient on whom the procedure is performed. For example, the length of the blade 20 can be approximately eight (8) inches for an adult patient and about four inches for a pediatric operation occurring at the same respective location. As one skilled in the art will appreciate, the dimensions of the blade 20, such as length, width, and thickness, can be designed for different, specific surgical procedures. Design considerations include the surgical procedure being performed, the required structural strength, the desired flexibility of the blade 20, and the predetermined area of the patient's body where the operation will occur.

As best shown in FIG. 1, at least a portion of the blade 20 is arcuate in cross section. This is preferred because a curved cross section is stronger and more stable than a flat profile. However, a blade 20 that is substantially rectangular in cross section is contemplated as an alternate embodiment.

Preferably, at least a portion of the edge 29 of the blade 20 immediately adjacent its distal end 26, or front tip, is arcuate. As FIG. 1 shows, the edge 29 of the front tip has a constant curvature along the edge 29 of the front tip. An alternate embodiment is more blunt, such as a front tip having a squared "C" shape (not shown) in which there is not a constant curvature along the front tip. The edge 29 of the front tip itself should be smooth and blunt-as opposed to having sharp corners-to reduce the chances of tissue damage or other injuries when used during the surgical procedure. For example, the blunt shape of the blade 20 can be used to repel tissue away from any areas of adhesiolysis and prevent trauma to the tissue.

The retractor 10, as noted above, is preferably designed for endoscopic use and includes the receptacle 30 for supporting a predetermined surgical instrument. The receptacle 30 is preferably disposed adjacent the bottom surface 24 of the blade 20. The preferred receptacle 30 comprises a longitudinally-extending tube 32 defining a passage 33 therethrough. The passage 33 is of a size to allow the predetermined endoscopic instrument to be slidably received therein. The diameter of the passage 33 is of an appropriate dimension to accommodate a particular endoscope or surgical instrument, such as a four (4) or five (5) millimeter diameter for standard endoscopic procedures, or a two (2) or three (3) millimeter diameter for pediatric surgery.

The tube 32 has an insertion end 34 disposed adjacent the proximal end 28 of the blade 20, an opposed operating end 36. The predetermined surgical instrument is slidably disposed into the insertion end 34, through the passage 33, and protrudes from (e.g., when using a cutting instrument) or is aligned with (e.g., when using an endoscope) the operating end 36. For using an endoscope, it is preferred that the operating end 36 of the tube 32 forms an angle φ relative to the normal N, or a perpendicular axis, to the longitudinal axis L or the bottom surface 24 of the blade 20. That is, a top outer surface 38 of the tube 32 at the operating end 36 is longer than a bottom outer surface 39 so that an angle φ exists relative to vertical, preferably an angle φ of thirty degrees (30°). Other angles φ can be used, but thirty degrees has been found acceptable because the endoscope provides an approximately thirty degree angle (30°) view below horizontal on the video monitor with this angle φ of thirty degrees (30°).

The retractor 10 also preferably further comprises a handle 40 having a first end 42 and an opposed second end 44. The second end 44 of the handle 40 is attached to the top surface 22 of the blade 20 adjacent its proximal end 28. The attachment of the blade 20 to the handle 40 may be accomplished by a permanent weld, or, as shown in FIG. 2, the blade may be connected by threads 47 on the interior of handle 40 and complementary threads 27 on the blade 20. In this way, while the blade 20 may be in a fixed position with respect to the handle 40, it may be replaced with another blade, if desired. The handle 40 defines a bore 46 extending therethrough extending from the first end 42 to the second end 44. The blade 20 also has an aperture near its proximal end 28 aligned, or in registry, with the bore 46 second end 44 of the handle 40.

Referring now to FIG. 2, the preferred connecting means comprises a ball 50 disposed within the bore 46 of the handle 40 adjacent its second end 44. A portion of the ball 50 is fixedly attached to a portion of the receptacle 30. The ball 50 is movably secured within the bore 46 so that the ball 50 and attached receptacle 30 are movable relative to the blade 20 without separating therefrom. As shown in FIG. 2, the ball 50 is movably secured because the opening through the blade 20 or the second end 44 of the handle 40 is smaller than the widest dimension of the ball 50. Accordingly, the ball 50 can rotate, pivot, or otherwise move within the bore 46 of the handle 40, but not traverse through the opening in the blade 20.

It is preferred that the ball 50 and the receptacle 30 are attached to each other by a connecting member 52. The connecting member 52 has opposed ends 54, 56, in which one end 54 is fixedly attached to the ball 50 and the opposed end 56 is fixedly attached to the receptacle 30. A portion of the connecting member 52 can be threaded (not shown) and complementarily received in a threaded hole (not shown) in the ball 50 to facilitate the assembly of the retractor 10 by joining the connecting member 52 to the ball 50 when the ball 50 is disposed within the bore 46 of the handle 40.

One locking means of the present invention comprises a shaft 60 and a means for adjustably positioning the shaft 60 within the bore 46 between an engaged position and a disengaged position. The shaft 60 has an upper end 62 and an opposite lower end 64 and at least a portion of the shaft 60 is complementarily received within the bore 46. Referring to FIG. 3, the lower end 64 is sized to complementarily and detachably engage a portion of the ball 50, specifically the upper portion. When in the engaged position, the lower end 64 of the shaft 60 detachably engages the ball 50 to frictionally hold the ball 50 and, when in the disengaged position, the lower end 64 of the shaft 60 and the ball 50 are spaced apart so that the ball 50 is movable. The lower end 64 of the shaft 60 and ball 50 do not need to be completely spaced apart to be in the disengaged position, but, instead, may be sufficiently separated to allow movement therebetween. That is, in the disengaged position, the lower end 64 of the shaft 60 and the ball 50 are adequately physically separated, or disengaged, so that the lower end 64 does not frictionally hold or lock the ball 50 in a non-movable position.

Another embodiment of the locking means shown in FIG. 2 includes a socket 66 that is attached to or contacted by the lower end 64 of the shaft 60. The socket 66 has an interior surface 68 of a size to complementarily engage an upper portion of the ball 50. Thus, in the engaged position, the interior surface 68 of the socket 66 detachably engages the ball 50 to frictionally hold the ball 50, instead of the lower end 64 of the shaft 60. That is, the lower end 64 of the shaft 60 is either attached to or pushes against the socket 66 causing the interior surface 68 to engage the ball 50. These shaft 60 designs are considered interchangeable and a primary consideration in deciding which to use is manufacturing costs.

Preferably, the means for positioning the shaft 60 also comprises a portion of the bore 46 complementarily engaging a portion of the shaft 60. The interface between the bore 46 and shaft 60 thereby controls the relative movement therebetween as the shaft 60 is moved within the bore 46. It is preferred that the portions of the bore 46 and the shaft 60 that engage each other are complementarily threaded surfaces 69, although other embodiments may be used, such as a protrusion (not shown) on the shaft 60 that traverses along a groove (not shown) formed in the bore 46 to maintain the shaft 60 in a selected one of the engaged or the disengaged positions.

Referring again to FIGS. 1–3, it is preferred that the shaft 60 further comprises a tightener 70 fixedly attached to the upper end 62 of the shaft 60 and disposed outside the bore 46. Rotation of the tightener 70 causes the shaft 60 (and separate socket 66 if used) to move between the engaged and disengaged positions, depending on the direction of rotation, because of the complementarily threaded surfaces 69 of the shaft 60 and bore 46 engaging each other. The tightener 70 also preferably has a plurality of notches 72 on its periphery therein to assist rotation of the tightener 70. The notches 72 are of a size to engage a portion of one of the surgeon's fingers.

It is also preferred that the surgical instrument use a compression fitting to be secured to the insertion end 34 of the tube 32. This is because a compression fitting allows longitudinal movement of the surgical instrument along the passage 33 of the tube 32 when the surgeon applies sufficient force. A bayonet-type endoscopic fitting (not shown) is another contemplated fitting formed at the insertion end 34 of the tube 32 to secure the predetermined surgical instrument at a desired position in the tube 32. Other securing devices known in the art can similarly be used. It is contemplated that the surgical instruments can be switched during the surgical procedure while stationarily maintaining the blade 20 at the surgical site, e.g., switching a suction instrument with an endoscope and vice versa.

Advantages of the present invention are highlighted by considering an example of its use. In one scenario, the surgeon, gripping the handle 40 of the retractor 10, starts the procedure by placing distal end 26 of the blade 20 into the body cavity where the surgical procedure will be performed. The endoscopic surgical instrument, specifically the endoscope in this example, is disposed within the receptacle 30 (which is locked in its initial position) and the surgeon views the video monitor while positioning the distal end 26 of the blade 20. When the retractor 10 is moved to the desired location, the surgeon can, if desired, rotate the tightener 70 using his thumb so that the ball 50 and socket 66 are in the disengaged position. With his other hand which is not gripping the handle 40, the surgeon can grab the insertion end 34 of the tube 32 or a portion of the endoscope to move the tube 32 and orient the camera. As one skilled in the art will appreciate, the ball 50 connection allows a great freedom of movement (e.g., up and down, side to side, and a combination thereof) relative to the blade 20. Once the camera is maneuvered to view a desired area of the surgical site, the surgeon can easily lock the endoscope into position by rotating the tightener 70 in the opposite direction, which places the locking means in the engaged position. With the preferred embodiment, the surgeon can move his thumb against the notches 72 in the tightener 70 to lock the endoscope in the selected desired position. This process of redirecting the endoscope occurs while the blade 20 of the retractor 10 remains stationary or, alternatively, the surgeon can move the blade 20 also. The surgeon can repeat the same actions throughout the surgical procedure whenever he desires to remove the endoscope (or other surgical instrument) being used. Of course, this is one example of use of the present invention and, as persons skilled in the art will appreciate, many other methods of using of the present invention exist.

Although the present invention has been described with reference to specific details of certain embodiments thereof, it is not intended that such details should be regarded as limitations upon the scope of the invention except as and to the extent that they are included in the accompanying claims.

What is claimed is:

1. A retractor, comprising:
    a. a longitudinally-extending blade having a top surface, a bottom surface, a distal end, an opposed proximal end, and an edge circumscribing said blade;
    b. a receptacle adapted to support a predetermined surgical instrument; and
    c. means for movably connecting said receptacle to said blade, wherein said connecting means allows said receptacle to move rotatable and pivotally relative to said blade to a selected one of a plurality of desired positions, wherein said receptacle is spaced apart from said connecting means.

2. The retractor of claim 1, further comprising a handle having a first end and an opposed second end, said second end fixedly attached to the top surface of said blade adjacent the proximal end thereof, said handle defining a bore extending therethrough.

3. The retractor of claim 1, wherein the receptacle comprises a longitudinally-extending tube defining a passage therethrough and having an insertion end disposed adjacent the proximal end of said blade, an opposed operating end, a top outer surface, and a bottom outer surface, said passage sized to allow a portion of a predetermined surgical instrument to be slidably received therein.

4. The retractor of claim 3, wherein the operating end of said tube forms an angle relative to a normal to the bottom surface of said blade so that said top outer surface is longer than said bottom outer surface.

5. The retractor of claim 1, wherein at least a portion of the edge of said blade adjacent the distal end thereof is arcuate.

* * * * *